(12) United States Patent
Georgeson et al.

(10) Patent No.: US 7,669,477 B2
(45) Date of Patent: Mar. 2, 2010

(54) ULTRASONIC PROBE FOR HOLLOW FUSE PIN INSPECTION

(75) Inventors: Gary Georgeson, Federal Way, WA (US); James Lee, Federal Way, WA (US); Mortenza Safai, Seattle, WA (US); Martin Freet, Federal Way, WA (US)

(73) Assignee: The Boeing Company, Chicago, IL (US)

( * ) Notice: Subject to any disclaimer, the term of this patent is extended or adjusted under 35 U.S.C. 154(b) by 520 days.

(21) Appl. No.: 11/615,505

(22) Filed: Dec. 22, 2006

(65) Prior Publication Data

US 2008/0148856 A1  Jun. 26, 2008

(51) Int. Cl.
*G01N 29/24* (2006.01)
*G01N 29/06* (2006.01)
(52) U.S. Cl. ........................................... 73/623
(58) Field of Classification Search .................. 73/623
See application file for complete search history.

(56) References Cited

U.S. PATENT DOCUMENTS

| | | | | |
|---|---|---|---|---|
| 3,952,581 A * | 4/1976 | Gottelt | ........................ | 73/640 |
| 4,306,459 A * | 12/1981 | Johnson et al. | ............... | 73/623 |
| 4,569,230 A * | 2/1986 | Asty et al. | ..................... | 73/623 |
| 4,586,380 A * | 5/1986 | Patterson | ..................... | 73/623 |
| 4,757,258 A | 7/1988 | Kelly, Jr. et al. | | |
| 4,864,862 A * | 9/1989 | Nottingham et al. | .......... | 73/623 |
| 5,189,915 A * | 3/1993 | Reinhart et al. | ............... | 73/623 |
| 5,254,944 A | 10/1993 | Holmes et al. | | |
| 5,272,734 A | 12/1993 | Clark et al. | | |
| 5,460,045 A | 10/1995 | Clark et al. | | |
| 5,479,100 A | 12/1995 | Fowler et al. | | |
| 5,503,019 A * | 4/1996 | Dewasmes | ................... | 73/623 |
| 5,574,223 A | 11/1996 | Kiefer | | |
| 5,641,909 A | 6/1997 | Kiefer et al. | | |
| 5,987,991 A | 11/1999 | Trantow et al. | | |
| 6,076,407 A | 6/2000 | Levesque et al. | | |
| 6,449,326 B1 * | 9/2002 | Walker et al. | ............... | 376/260 |

* cited by examiner

*Primary Examiner*—Hezron Williams
*Assistant Examiner*—Rose M Miller
(74) *Attorney, Agent, or Firm*—Brosemer, Kolefas & Associates

(57) ABSTRACT

A self-aligning probe assembly has one or more ultrasonic transducers adapted to transmit an ultrasonic shear wave into the inside surface of the hollow structure such as an aircraft fuse pin and to receive the shear wave emerging from the inside surface of the hollow structure. The nature of the received shear wave indicates the presence of flaws or damage in the inspected part. The probe assembly can be used to inspect fuse pins on aircraft without having to remove the aircraft engines.

13 Claims, 6 Drawing Sheets

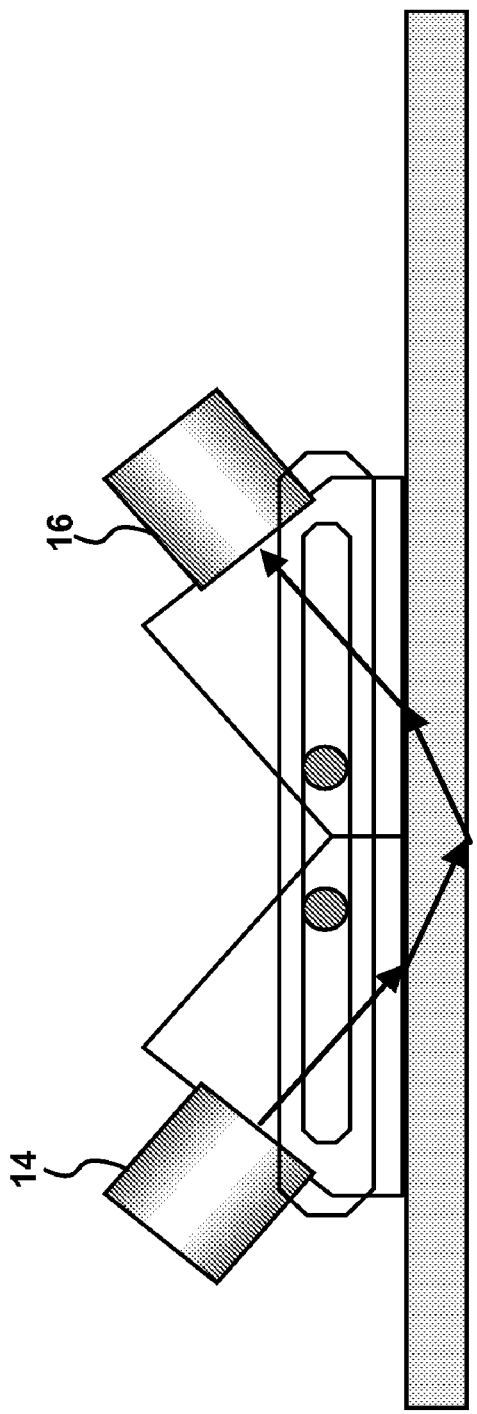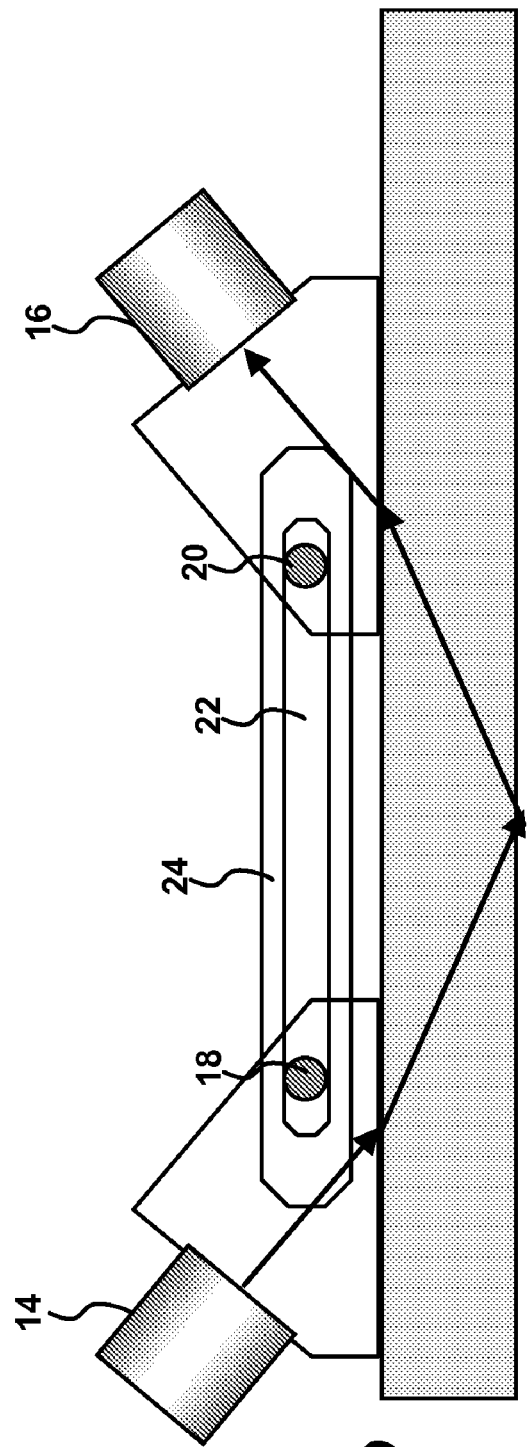

ULTRASONIC PROBE FOR HOLLOW FUSE PIN INSPECTION

TECHNICAL FIELD

This disclosure relates to inspection of parts for defects or damage. More particularly, this disclosure relates to ultrasonic inspection of hollow structures such as aircraft fuse pins.

BACKGROUND

During hard landings, the hollow fuse pins that hold the engines onto some aircraft such as the KC-135 can be damaged and need to be inspected. The typical damage is an outer diameter (OD) crack or offset (step), or a gradual bending. Currently, the pin must be removed in order to inspect for these types of damage, which requires significant labor and time. A prime example of where this is a significant problem is the KC-135 aircraft. These aircraft have four fuse pins on every strut: over-wing, at the diagonal brace, and mid-spar, all of which need to be inspected. While an optical in-bore method has been conceived to measure bending of the pins and offsets down to less than 0.005", no method currently exists to find the OD cracks with the pins still mounted.

SUMMARY

A device and method in accordance with the invention allows for on-aircraft ultrasonic inspection of engine hollow fuse pins for OD circumferential cracks and offsets caused by hard landings. This is a rapid, low cost method to inspect fuse pins without removing engines which will save significant maintenance and inspection costs. The device and method of the invention also can be used to inspect other kinds of hollow structures.

BRIEF DESCRIPTION OF THE DRAWINGS

FIGS. 2a and 2b illustrate lateral adjustment of the ultrasonic transmitter and ultrasonic receiver in the probe assembly of FIG. 1.

DETAILED DESCRIPTION

Figure 1A:
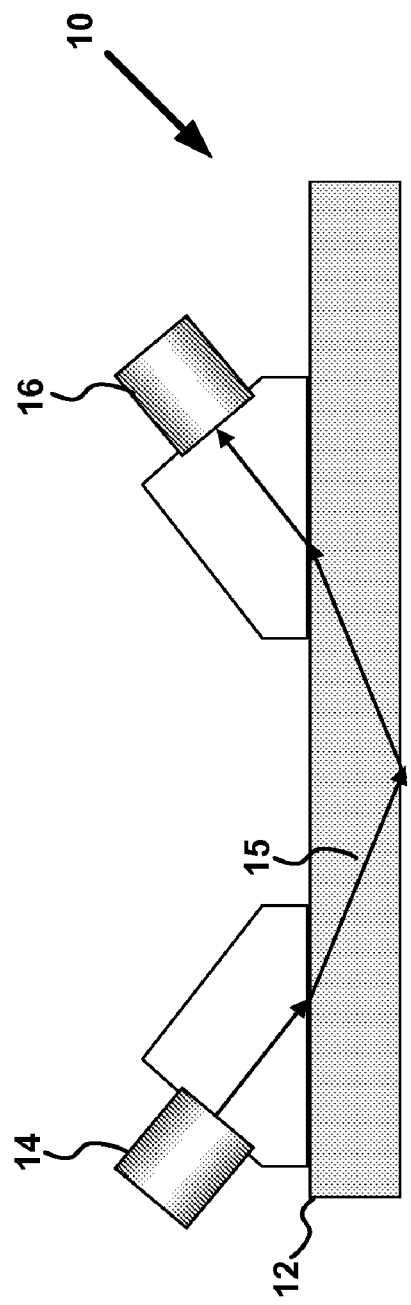
FIGS. 1a and 1b illustrate the principles used by the invention to ultrasonically inspect for cracks and other damage in aircraft fuse pins.
Figure 1B:
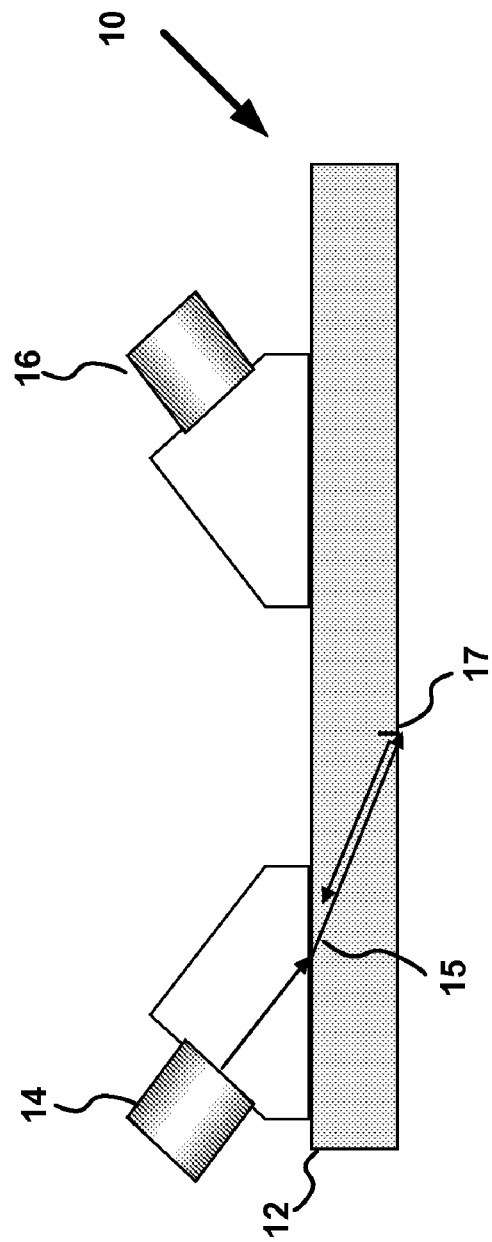

Fuse pin circumferential crack inspection involves an ultrasonic shear wave probe assembly shown generally at reference numeral 10 in FIGS. 1a and 1b. Cracks and other damage in a metal structure 12 may often be found using shear wave ultrasonic-based inspection in accordance with this invention. With this technique, an ultrasonic stress wave is produced by a transducer 14 containing a piezoelectric material that receives an electric pulse from an ultrasonic test system not shown in FIGS. 1a and 1b. The transducer 14 can be mounted so as to insert the stress wave 15 into adjacent structure 12. If it is mounted at an angle, a particular type of stress wave called a "shear wave" or "S-wave" is produced that has a shearing type of action as it travels through a material of the structure 12. The shear wave will reflect and/or transmit at impedance boundaries according to the laws of wave physics. As shown in FIG. 1a, when the structure 12 is flawless, the magnitude and phase of the shear wave can be sensed using an appropriately positioned second ultrasonic transducer 16 that picks up the signal and converts it back into an electric signal, for measurement and analysis in the ultrasonic test system. When the structure 12 contains a crack or other defect 17, as in FIG. 1b, the shear wave 15 is partially or completely reflected or scattered by the flaw and thus either is not received by the sensor 16 or is received at reduced amplitude, an event recognized by the ultrasonic test system as area of damage or other flaw.

The displacement between the transducers 14 and 16 may be horizontally adjusted, as shown in FIGS. 2a and 2b. The displacement between the transducers 14 and 16 should be such that the transducer 16 receives a sufficient amplitude signal from transducer 14 when a good part is being inpected. The thickness of the part under inspection and the transmission and reflection angles will determine the appropriate distance between transducers 14 and 16.

As discussed above, the presence of a flaw will reduce the amplitude of the signal from transducer 14 received by transducer 16. An adjustable fitting 24 can hold the probes 14 and 16 at the selected distance. The horizontal adjustment mechanism for the probe assembly of FIGS. 2a and 2b comprises a pin 18 on probe 14 and a pin on probe 16 that ride in a slot 22 formed in the fitting 24 of the probe assembly 10.

The invention is not limited to use with any particular ultrasonic transducer. For example, the transducers 14 and 16 may be ultrasonic transducers made by Krautkramer. The transducers 14 and 16 may be part of an ultrasonic test system such as a USN 60 ultrasonic flaw dedector also made by Krautkramer.

Figure 3A:
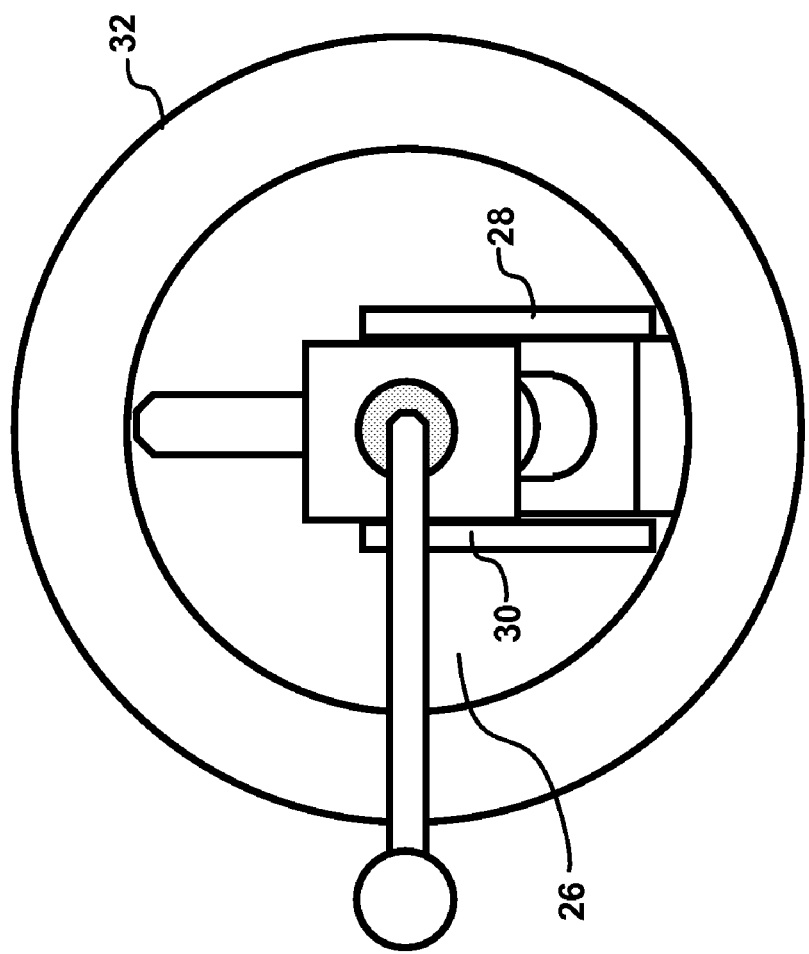
FIGS. 3 and 3a illustrate an embodiment of the invention involving a hand turned ultrasonic probe.
Figure 3B:
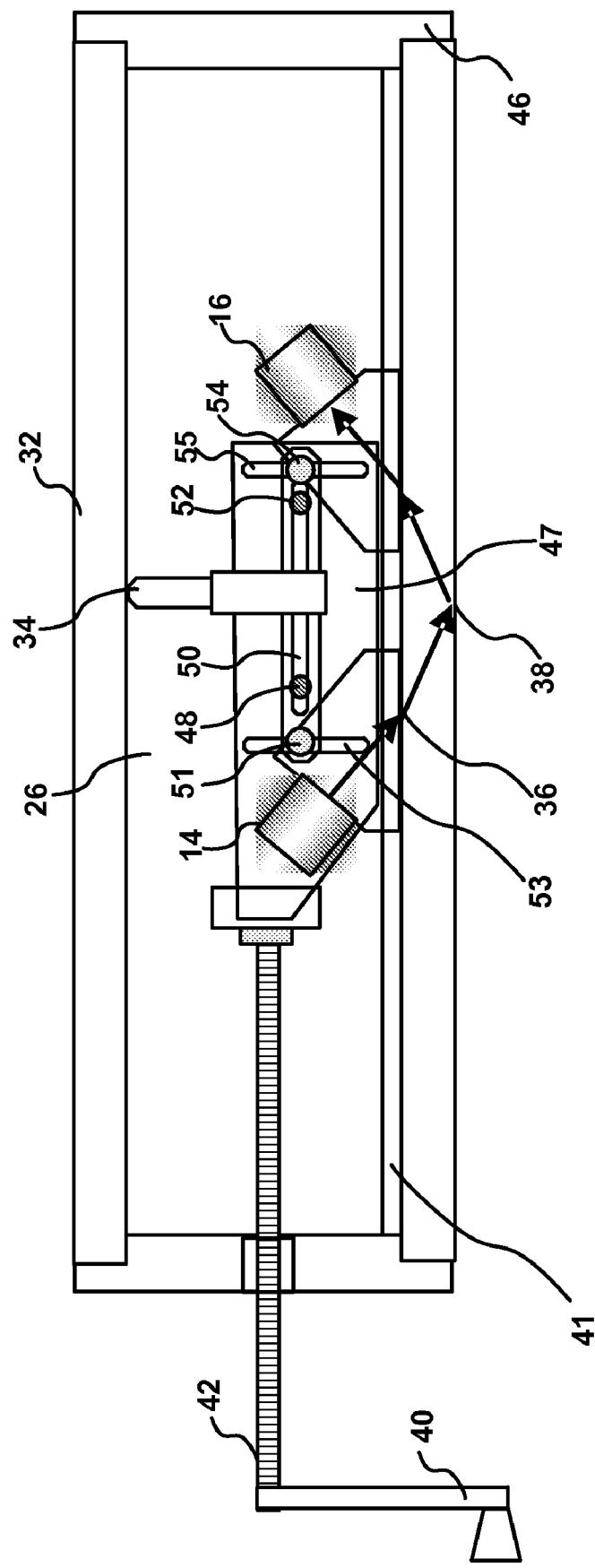

In one particular embodiment of the invention shown in FIG. 3, a self-aligning inspection probe assembly 26 that contains a sending ultrasonic transducer 14 and a receiving ultrasonic transducer 16. The transducers 14 and 16 are mounted on shoes 28 and 30 pressed against a portion of the inner diameter of a cylindrical fuse pin 32 using a spring loaded standoff 34 which presses against a diametrically opposite portion of the inner diameter of the fuse pin 32 to align the probe assembly 26 inside the fuse pin 32. The probe assembly 26 is designed to fit inside the hollow fuse pin 32, and will self-align and self-center inside the fuse pin 32, for proper orientation of the transducers 14 and 16, as shown most clearly in FIG. 3a.

The ultrasonic signal from the "sending" transducer 14 enters the pin wall 36 at an angle, bounces off the outer wall 38, and returns to the "receiving" transducer 16. A circumferential crack will provide a barrier to the shear wave traveling between transducers 14 and 16, and will reduce the signal amplitude at the receiving transducer 16 and the corresponding electrical signal output by the transducer 16.

The probe end holding the transducers may be rotated 360 degrees around the inside of the pin 32, and carefully indexed axially to cover all potentially damaged areas of the fuse pin 32. This can be done by hand using the handle or crank 40 at the end of a threaded rod or screw 42, extending through a rubber end cap 44, which allows for the rotation and advancement of the probe assembly completely around and through the fuse pin 32. The inspector visually monitors the ultrasonic test equipment display (or sets an audible or visual alarm) for a pre-determined drop in the amplitude. The amount of ultrasonic amplitude drop is pre-determined using a calibration standard with known crack sizes.

The transducer mount 47 supporting the transducers 14 and 16 in the assembly 26 provides the capability of adjusting the location of the transducers 14 and 16 axially and radially in the inside of the fuse pin 32. The transducer 14 in FIG. 3 can be adjusted axially in the assembly 26 by means of a pin 48 fixed to the transducer 14 that slides in a slot 50 formed in the transducer mount 47. The transducer 14 in FIG. 3 can be also adjusted radially in the assembly 26 by means of a pin 51 fixed to the transducer 14 that slides in a slot 53 in the mount 47. The transducer 16 in FIG. 3 can be adjusted axially by means of a pin 52 fixed to the transducer 16 that slides in the slot 50 and radially by means of a pin 54 fixed to the transducer 16 that slides in the slot 55. The pins 48, 51, 52, and 54 may be threaded members that each have a nut that is used to tighten its respective rod to the mount 47 to fix the location of the transducers 14 and 16 in the assembly 26 after adjustment.

A liquid or gel couplant may be used to get the ultrasonic stress wave more effectively from the probe assembly 26 into and out of the structure being tested. There are several options. A gel specially designed for ultrasonic testing can be squirted into the center of the pin, and spread around so that the shoes always have couplant between them and the pin wall. This gel would need to be cleaned out after the test. Or, a grease can be used that can be left in the pin. The rubber end caps 44 and 46 with threaded sleeves in FIG. 3 can be used to hold a bath of water or other liquid couplant that will wet the transducers each time they rotate through it. Or, when end caps are not desired, water can be dribbled out through a hole at the end of the shoe using low pressure water fed through a plastic tube. In this case, the inspector would need to have a means to control the water draining out of the pin, with rags or some sort of a makeshift dam at the sides of the pin.

Figure 4:
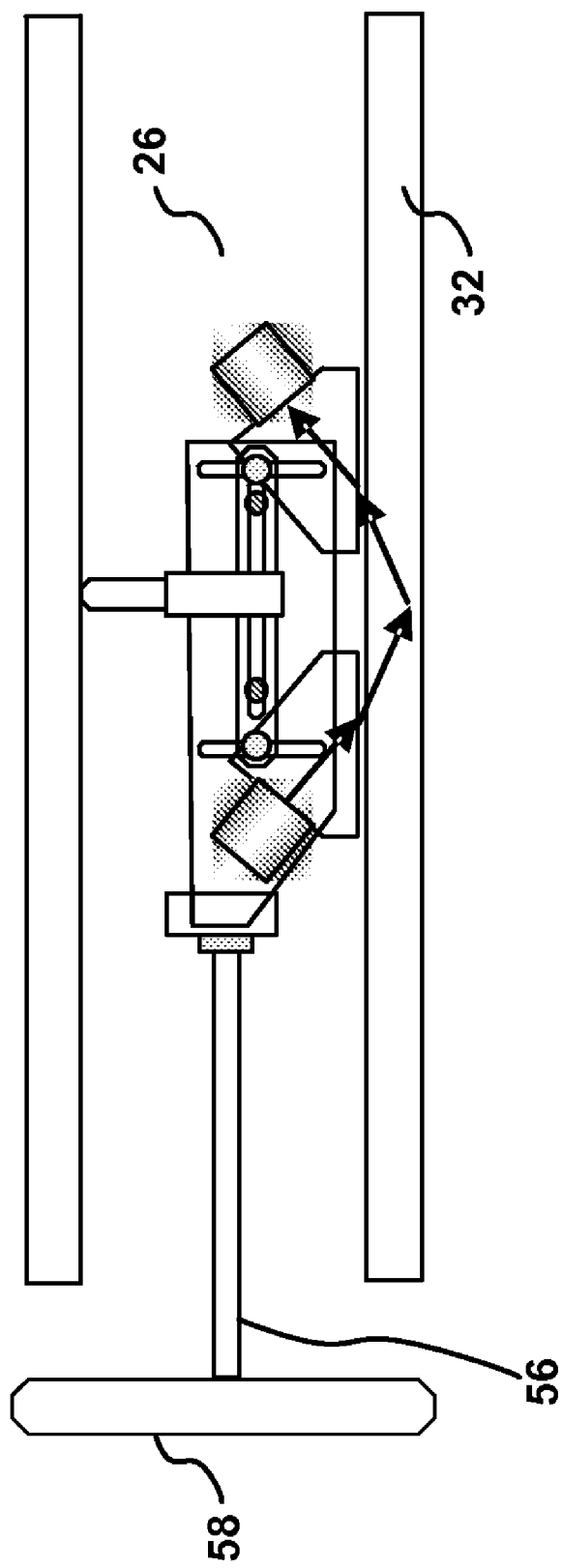
FIG. 4 illustrates an embodiment of the invention involving another hand turned ultrasonic probe.

A second embodiment of the invention is shown in FIG. 4, which is a hand-held (non-screw) concept of ultrasonic bore inspection tool. The tool can be moved axially or circumferentially by hand. End caps can also be used to contain a couplant bath in the fuse pin 32 to keep the couplant from dripping out during inspection. The same inspection can be done with a hand-held system without the end caps or a hand crank. In this embodiment, the probe assembly 26 is held at one end of an unthreaded rod 56. The other end of the rod 56 has a handle 58 held by the operator when the probe assembly 26 is inserted into the fuse pin 32 and slid axially from one end of the fuse pin 32 to the other end of the fuse pin 32. In addition to being slid axially toward one end or the other of the fuse pin 32, the probe assembly 26 is also rotated circumferentially around the inside of the fuse pin 32 at each axial location to search for defects on the entire inside of the fuse pin 32.

Figure 5:
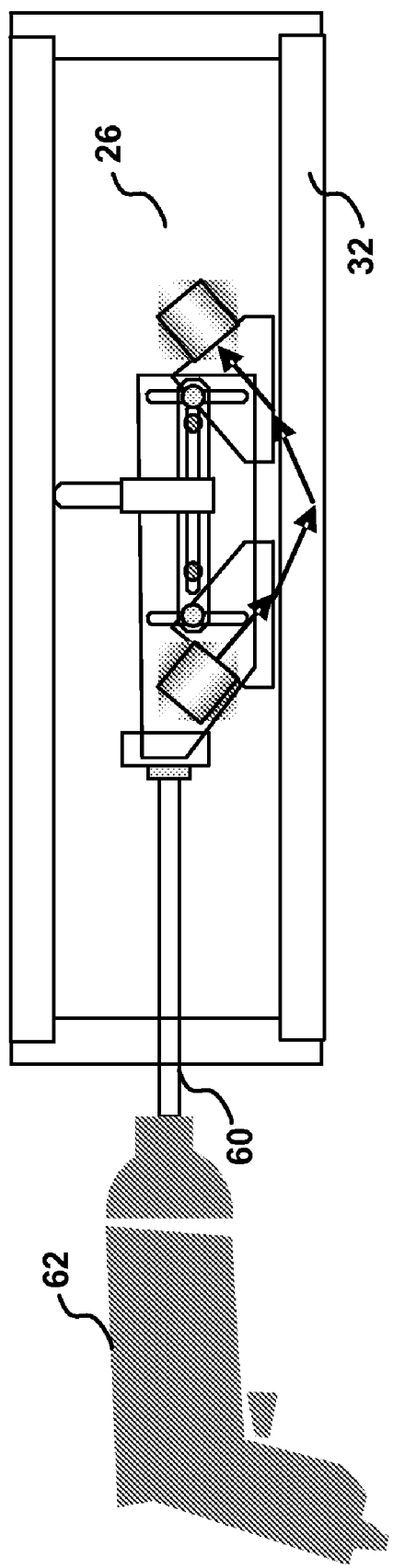
FIG. 5 illustrates an embodiment of the invention involving motorized turning of an ultrasonic probe.

A third embodiment of the invention shown in FIG. 5 which involves mounting the probe assembly 26 on a rod 60 that is rotated with a low speed drill-type motor 62. This approach is the least operator-dependent, and the quickest, but requires battery or A/C power.

It should be noted that an alternative configuration requiring only a single transducer used in a pulse-echo mode is possible. This configuration can be used with any of the three embodiments. Instead of setting up a test to look for loss of transmitted signal amplitude, the operator sets up the test to look for any return signal within a certain time frame. No signal will be returned in a "good" area, but a crack will produce a reflection that will be picked up by the single transducer. Dual transducer, pitch-catch configurations shown in FIGS. 1-5 are preferred for this type of inspection, however, since they are generally more reliable than single transducer implementations. The reason for this is that if a single transducer is set up incorrectly, a lack of signal will not necessarily indicate a good part.

Advantages of rotating shear wave probe in accordance with this invention include the fact that the probe assembly 26 can be attached to an off-the-shelf existing ultrasonic test system, such as the Krautkramer USN 60 ultrasonic test system mentioned above. A probe in accordance with this invention is a low cost, rapid solution to the problem of finding both internal and external cracks in hollow cylindrical structures such as aircraft fuse pins. As described above, the probe can be rotated by hand or attached to a crank or drill motor. The probe can be used to inspect different size hollow structures. For example, fuse pins with a range of inside diameters from about 0.6" to 1.1" can be inspected. The probe can also be configured to inspect other hollow structures, such as piping and conduits.

The Title, Technical Field, Background, Summary, Brief Description of the Drawings, Detailed Description, and Abstract are meant to illustrate the preferred embodiments of the invention and are not in any way intended to limit the scope of the invention. The scope of the invention is solely defined and limited by the claims set forth below.

The invention claimed is:

1. A self-aligning ultrasonic probe assembly for inspecting a hollow structure, comprising:
    a first ultrasonic transducer adapted to transmit an ultrasonic shear wave into the hollow structure;
    a second ultrasonic transducer displaced from the first transducer and adapted to receive the ultrasonic shear wave transmitted into the hollow structure;
    a mounting adapted to hold the first and second ultrasonic transducers in predetermined positions in the hollow structure, the mounting having a mechanism adapted to permit adjustment of the displacement of the first transducer with respect to the second transducer, and;
    an alignment mechanism adapted to be in contact with opposed portions of the inside surface of the hollow structure to align the probe assembly in the hollow structure.

2. The probe assembly of claim 1, further comprising:
    a mechanism for rotating the probe assembly.

3. The probe assembly of claim 2, in which the mechanism for rotating the probe assembly comprises a hand crank.

4. The probe assembly of claim 2, in which the mechanism for rotating the probe assembly comprises:
    a rod extending from the probe assembly.

5. The probe assembly of claim 2, in which the mechanism for rotating the probe assembly comprises an electric motor.

6. The probe assembly of claim 2, in which the mechanism for rotating the probe assembly comprises a hand drill.

7. The ultrasonic probe assembly of claim 1, further comprising an ultrasonic test system connected to the first and second ultrasonic transducers.

8. A method of inspecting a fuse pin on an aircraft, comprising the steps of:
    inserting the self aligning probe assembly of claim 1 into an aircraft fuse pin holding an aircraft engine on an aircraft while the engine is on the aircraft; and
    moving the probe assembly axially and circumferentially in the interior of the fuse pin to inspect the fuse pin for flaws or damage.

9. The method of claim 8, further comprising the step of:
    coating the interior of the fuse pin with a couplant that facilitates the entry and exit of ultrasonic energy into and out of the fuse pin.

10. The probe assembly of claim 1, in which the adjustment mechanism in the mounting is adapted to permit adjustment of the horizontal displacement of one of the first and second transducers with respect to the other of the first and second transducers.

11. The probe assembly of claim 1, in which the adjustment mechanism in the mounting is adapted to permit adjustment of the axial and radial positions of the first and second transducers in the hollow structure.

12. The probe assembly of claim 10, in which the adjustment mechanism comprises a pin on at least one of the first and second transducers riding in or more slots on the probe assembly.

13. The probe assembly of claim 11, in which the adjustment mechanism comprises a pin on at least one of the first and second transducers riding in or more slots on the probe assembly.

* * * * *